US010964021B2

(12) United States Patent
Aoyama et al.

(10) Patent No.: US 10,964,021 B2
(45) Date of Patent: Mar. 30, 2021

(54) INFORMATION PROCESSING APPARATUS, INFORMATION PROCESSING METHOD, AND INFORMATION PROCESSING SYSTEM

(71) Applicant: CANON KABUSHIKI KAISHA, Tokyo (JP)

(72) Inventors: Gakuto Aoyama, Kyoto (JP); Ryo Ishikawa, Kawasaki (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 130 days.

(21) Appl. No.: 16/259,925

(22) Filed: Jan. 28, 2019

(65) Prior Publication Data

US 2019/0251690 A1 Aug. 15, 2019

(30) Foreign Application Priority Data

Feb. 9, 2018 (JP) ............................ JP2018-022068

(51) Int. Cl.
*G06K 9/00* (2006.01)
*G06T 7/00* (2017.01)
*G16H 30/40* (2018.01)

(52) U.S. Cl.
CPC .......... *G06T 7/0016* (2013.01); *G16H 30/40* (2018.01); *G06T 2207/10081* (2013.01); *G06T 2207/30168* (2013.01)

(58) Field of Classification Search
CPC ............ G06T 7/00; G06T 2207/30096; G06T 2207/20224; G06T 2207/30168;
(Continued)

(56) References Cited

U.S. PATENT DOCUMENTS 7,869,664 B2 * 1/2011 Lu ......................... G01R 33/46 382/294
8,368,815 B2 * 2/2013 Tsurumi ............ G06K 9/00335 348/699

(Continued)

FOREIGN PATENT DOCUMENTS

JP 2013-126575 A 6/2013
WO WO-2005120353 A1 * 12/2005 ............... G06T 5/50
WO WO-2010037233 A1 * 4/2010 ............ A61B 5/055

*Primary Examiner* — Mahendra R Patel
(74) *Attorney, Agent, or Firm* — Canon U.S.A., Inc IP Division

(57) ABSTRACT

An information processing apparatus includes a first selection unit that selects a second image to be compared with a first image from a plurality of candidate images, a setting unit, an overlap range calculation unit, an evaluation value calculation unit, and a second selection unit. The setting unit sets a plurality of combinations including two or more candidate images from among the plurality of candidate images. The overlap range calculation unit calculates an overlap range between the first image and each of the plurality of combinations. The evaluation value calculation unit calculates an evaluation value of each of the plurality of combinations based on the calculated overlap range. The second selection unit selects at least one combination from the plurality of combinations based on the evaluation value. The first selection unit selects the two or more candidate images included in the selected combination as the second image.

11 Claims, 6 Drawing Sheets

400 410 420 430 450

(58) Field of Classification Search
CPC ........ G16H 30/40; G16H 40/20; G16H 30/20; G16H 50/20; H04N 5/14; H04N 5/341; H01L 21/67; G06K 9/46; G06K 9/62; G06K 9/4614; G06K 9/627; G06K 9/6234; G06K 2009/006; G06K 2009/00932; G06K 9/00013; G06K 9/00033; G06K 9/00335
USPC .................. 382/130, 201, 195, 203; 348/246
See application file for complete search history.

(56) References Cited

U.S. PATENT DOCUMENTS

2002/0097901 A1* 7/2002 Xu ........................... G06T 5/50 382/131
2008/0044066 A1* 2/2008 Miura ..................... G06K 9/20 382/124
2009/0185729 A1* 7/2009 Matsue .................... G06T 7/38 382/128
2012/0082389 A1* 4/2012 Sakamoto .......... H04N 5/23219 382/224
2012/0121141 A1* 5/2012 Miura ................ G06K 9/00033 382/115
2013/0040337 A1* 2/2013 Matsui .................. G01N 21/31 435/34
2014/0184774 A1* 7/2014 Miura ..................... G06K 9/20 348/77
2015/0012316 A1* 1/2015 Kakimoto ............. G06Q 50/02 705/7.11
2015/0189107 A1* 7/2015 Murata ................. H04N 1/387 345/629
2015/0206029 A1* 7/2015 Chikano ............. G06K 9/6211 382/201
2015/0350579 A1* 12/2015 Shiozaki ............. H04N 5/3675 348/246
2016/0253460 A1* 9/2016 Kanada .................. G16H 15/00 705/2
2017/0337697 A1* 11/2017 Kunihiro .............. G06K 9/4642
2018/0082455 A1* 3/2018 Yamaji ............... G06K 9/00684
2019/0385324 A1* 12/2019 Kume .................. G01B 11/002

* cited by examiner

INFORMATION PROCESSING APPARATUS, INFORMATION PROCESSING METHOD, AND INFORMATION PROCESSING SYSTEM

BACKGROUND

Field

The present disclosure relates to an information processing apparatus, an information processing method, and an information processing system.

Description of the Related Art

In a medical field, a medical doctor performs diagnosis using medical images captured by various modalities. In particular, in order to follow up a state of a subject, a medical doctor observes temporal changes of the subject by comparing a plurality of images captured by the same modality at different times. As a method for supporting observation of temporal changes of a subject, for example, there is a method described in Japanese Patent Laid-Open No. 2013-126575. Japanese Patent Laid-Open No. 2013-126575 discloses a technique where an image processing apparatus presents an image (hereinafter referred to as a subtraction image) obtained by drawing a difference between an image to be diagnosed (hereinafter referred to as a diagnosis object image) and an image to be compared (hereinafter referred to as a comparison image) and thereby a temporal change of a subject is emphatically displayed.

However, in an actual medical treatment, when observing a temporal change of a subject by comparing a plurality of images, it is a troublesome operation to select an appropriate comparison image from a plurality of images captured at different time points.

SUMMARY

An information processing apparatus, which includes a first selection unit that selects a second image to be compared with a first image from a plurality of candidate images, includes a setting unit that sets a plurality of combinations including two or more candidate images from among the plurality of candidate images, an overlap range calculation unit that calculates an overlap range between the first image and each combination of the plurality of combinations, an evaluation value calculation unit that calculates an evaluation value of each combination of the plurality of combinations based on the calculated overlap range, and a second selection unit that selects at least one combination from the plurality of combinations based on the evaluation value. The first selection unit selects the two or more candidate images included in the selected combination as the second image.

Further features will become apparent from the following description of exemplary embodiments with reference to the attached drawings.

DESCRIPTION OF THE EMBODIMENTS

The medical information processing apparatus according to the embodiment provides the functions described below to a user such as a medical doctor and a medical radiology technician in a medical institution. Specifically, the medical information processing apparatus performs comparison processing between a diagnosis object image and a comparison image related to a target patient (subject), on which the user intends to perform medical treatment, and provides a result of the comparison processing to the user. In the embodiment, a case will be described where there is a plurality of images (hereinafter referred to as comparison candidate images) captured by imaging the same subject at time points different from a time point of capturing the diagnosis object image. The medical information processing apparatus selects an image suitable to be compared with the diagnosis object image as the comparison image from among the plurality of comparison candidate images and performs the comparison processing between the diagnosis object image and the comparison image. Here, the comparison processing is, for example, processing of displaying each image so that a user can compare each image and processing of calculating the subtraction image by performing subtraction processing between images.

For example, for a certain subject, there is a case of trying to grasp occurrence or progression of a lesion of the subject by comparing an inspection image captured at the present time point (which is defined as the diagnosis object image in the embodiment) with an inspection image captured at a past time point (which is defined as the comparison image in the embodiment). In this case, it is desirable that imaging conditions are the same between these images. In particular, when a user tries to find a lesion in an organ (hereinafter referred to as an organ of interest) in the subject by comparing the diagnosis object image with the comparison image, it is desirable that an image of the organ of interest in both images is captured with the same imaging condition. However, in general, the inspection image is captured with an imaging condition appropriate for an inspection purpose, so that when the inspection purposes of each inspection image are different, the imaging conditions of each inspection image are different even when the inspection images are captured from the same subject. In the embodiment, a case is assumed where there is no comparison candidate image captured with an imaging condition of "the entire organ of interest is included in an imaging range." In other words, the embodiment illustrates an example where, in such a case, the medical information processing apparatus combines a plurality of comparison candidate images captured with an imaging condition of "A part of the organ of interest is included in the imaging range" and performs comparison processing between the diagnosis object image and the combination of the plurality of comparison candidate images.

Figure 1:
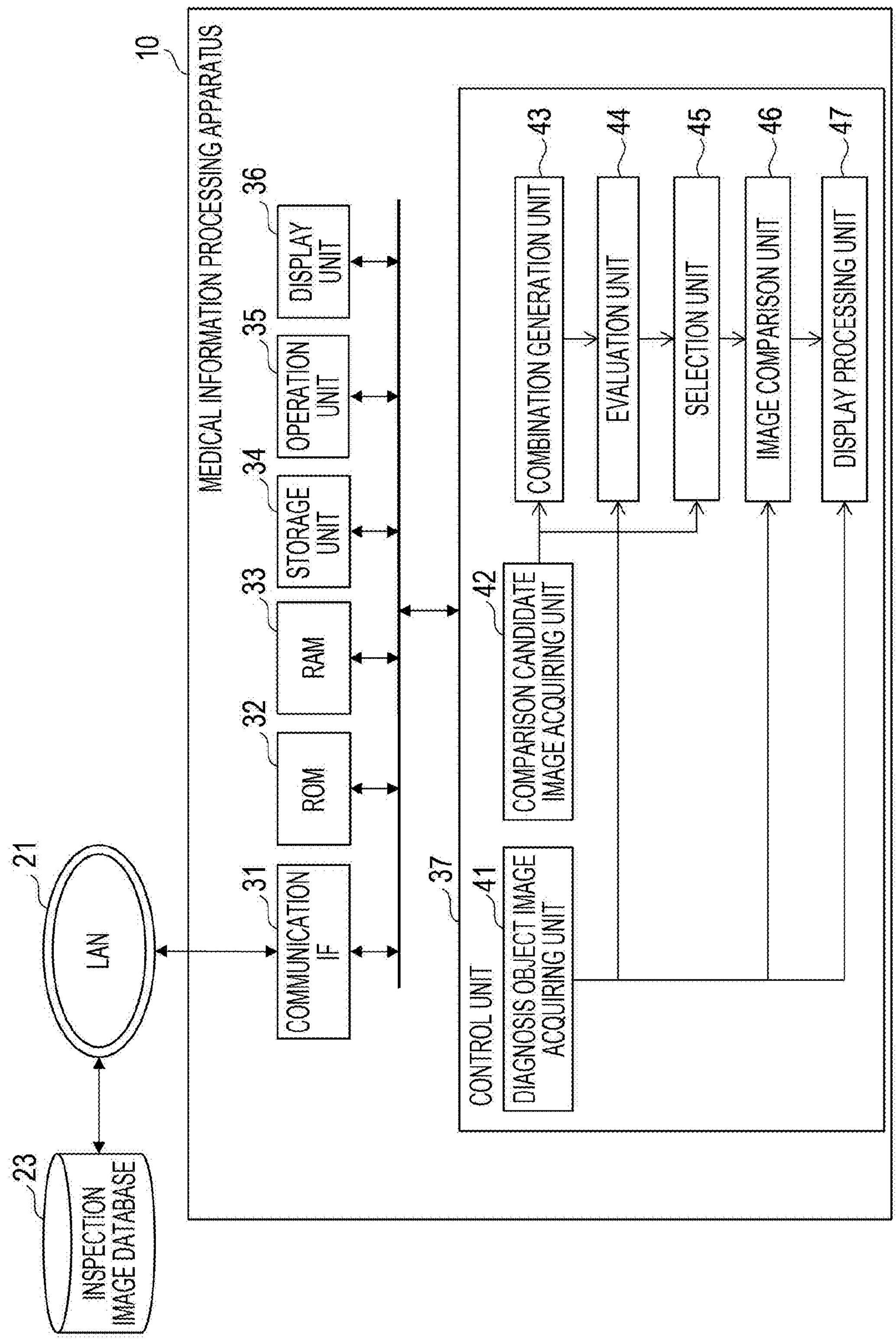
FIG. 1 is a diagram illustrating an equipment configuration of a medical information processing system according to an embodiment.

FIG. 1 is a diagram illustrating an overall configuration of a medical information processing system according to the embodiment. The medical information processing system includes a medical information processing apparatus 10 (corresponding to an information processing apparatus of the present disclosure) and an inspection image database 23, and the information processing apparatus 10 and the inspection image database 23 are communicably connected to each other via a communication unit. In the embodiment, the communication unit is composed of LAN (Local Area Network) 21. However, the communication unit can be composed of WAN (Wide Area Network). The connection method of the communication unit can be a wired or wireless connection.

The inspection image database 23 stores a plurality of inspection images related to a plurality of patients and accompanying information of the inspection images. The inspection image is a medical image captured by an image diagnosis apparatus such as, for example, a CT apparatus and an MRI apparatus, and various images such as a two-dimensional image, three-dimensional image, a monochrome image, and a color image are used as the inspection image. The accompanying information of the inspection images is information such as an ID of a patient (patient ID), an inspection date, an imaged region, an image reconstruction function, and imaging parameters including a tube voltage value, a tube current value, and the like. In addition to these, an inspection purpose, a name of an organ to be inspected, a name of a disease to be inspected, and the like may be included in the accompanying information. A unique identifier (hereinafter referred to as an inspection ID) is attached to each inspection image and the accompanying information thereof in order to identify the inspection image and the accompanying information thereof from other information, and information is read by the medical information processing apparatus 10 based on the inspection ID. When the inspection image is a three-dimensional volume image including a plurality of two-dimensional cross-sectional images (tomographic images), an inspection ID is attached to each two-dimensional cross-sectional image (tomographic image) and the three-dimensional volume image which is an aggregate of the two-dimensional cross-sectional images. The inspection image database 23 provides functions such as a list display of inspection images, a thumbnail display, search, and writing of information in cooperation with the medical information processing apparatus 10, in addition to the reading of information. In the embodiment, an image indicates image data.

The medical information processing apparatus 10 acquires information stored by the inspection image database 23 through the LAN 21. The medical information processing apparatus 10 includes a communication IF 31, a ROM 32, a RAM 33, a storage unit 34, an operation unit 35, a display unit 36, and a control unit 37 as functional components thereof.

The communication IF (Interface) 31 is realized by, for example, a LAN card or the like, and manages communication between the medical information processing apparatus 10 and an external apparatus (for example, the inspection image database 23) through the LAN 21. The ROM (Read Only Memory) 32 is realized by a non-volatile memory or the like and stores various programs. The RAM (Random Access Memory) 33 is realized by a volatile memory or the like and temporarily stores various information. The storage unit 34 is realized by, for example, HDD (Hard Disk Drive) or the like and stores various information. The operation unit 35 is realized by, for example, a keyboard, a mouse, and the like, and inputs an instruction from a user into the apparatus. The display unit 36 is realized by, for example, a display or the like, and displays various information to a user (for example, a medical doctor). The operation unit 35 and the display unit 36 provide a function as a graphical user interface (GUI) by control from the control unit 37.

The control unit 37 is realized by, for example, a CPU (Central Processing Unit) and the like, and integrally controls processing in the medical information processing apparatus 10. The control unit 37 includes a diagnosis object image acquiring unit 41, a comparison candidate image acquiring unit 42, a combination generation unit 43, an evaluation unit 44, a selection unit 45, an image comparison unit 46, and a display processing unit 47 as functional components thereof.

The diagnosis object image acquiring unit 41 acquires an inspection image of a patient as a diagnosis object image from the inspection image database 23 through the communication IF 31 and the LAN 21 based on to an operation of a user inputted from the operation unit 35. Then, the diagnosis object image acquiring unit 41 outputs the acquired diagnosis object image to the evaluation unit 44, the image comparison unit 46, and the display processing unit 47.

The comparison candidate image acquiring unit 42 acquires a plurality of inspection images (comparison candidate images), which will be candidates of a comparison image for the diagnosis object image acquired by the diagnosis object image acquiring unit 41, from the inspection image database 23 through the communication IF 31 and the LAN 21. Then, the comparison candidate image acquiring unit 42 outputs the plurality of acquired comparison candidate images to the combination generation unit 43 and the selection unit 45.

The combination generation unit 43 generates one or more combinations from the plurality of comparison candidate images acquired by the comparison candidate image acquiring unit 42. Then, the combination generation unit 43 outputs the generated combinations of the comparison candidate images to the evaluation unit 44.

The evaluation unit 44 calculates an evaluation value related to appropriateness of comparison with the diagnosis object image for each combination of the comparison candidate images generated by the combination generation unit 43. Then, the evaluation unit 44 outputs the calculated evaluation values to the selection unit 45.

The selection unit 45 selects a combination of the comparison candidate images to be compared with the diagnosis object image from the combinations of the comparison candidate images based on the evaluation values. In the description below, the selected combination of the comparison candidate images is referred to as a set of comparison images and the comparison candidate images included in the set of comparison images are referred to as comparison images. Then, the selection unit 45 outputs the set of comparison images to the image comparison unit 46.

The image comparison unit 46 performs the comparison processing between the diagnosis object image and the set of comparison images, and outputs a comparison result of the comparison processing to the display processing unit 47.

The display processing unit 47 displays the comparison result of the image comparison unit 46 on the display unit 36.

At least some of the units included in the control unit 37 can be realized as independent apparatuses. Each unit can be realized as software that realizes a function. In this case, the software that realizes a function can operate on a server through a network such as cloud. In the embodiment, each unit is realized by software in a local environment.

The configuration of the medical information processing system illustrated in FIG. 1 is only an example. For example, the storage unit 34 of the medical information processing apparatus 10 can have a function of the inspection image database 23 and the storage unit 34 can hold a plurality of inspection images related to a plurality of patients and accompanying information of the inspection images.

Figure 2:
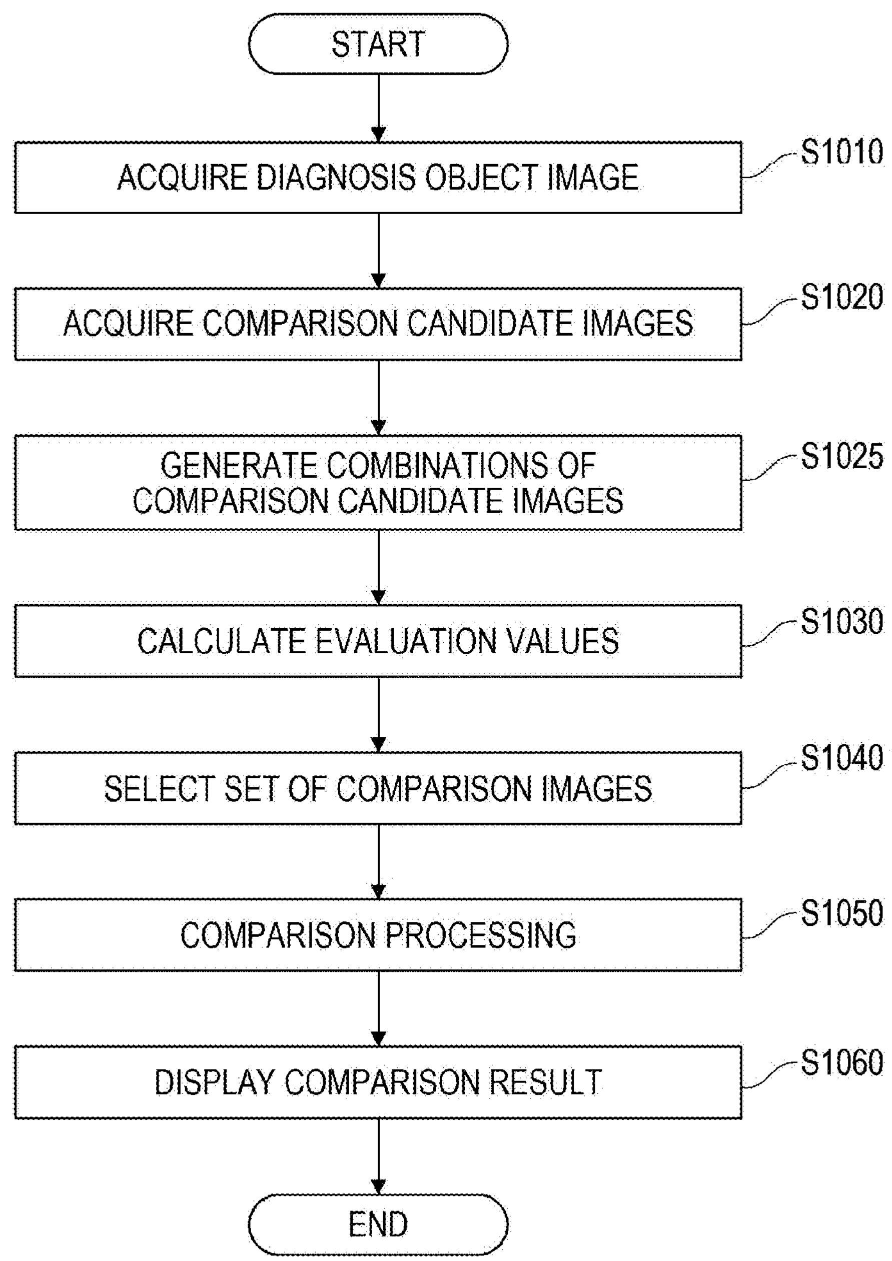
FIG. 2 is a flowchart illustrating an entire processing procedure in the embodiment.

Next, an entire processing procedure of the medical information processing apparatus 10 in the embodiment will be described in detail with reference to FIG. 2. In the description below, a case where a CT image is used as the inspection image is described as an example. However, the present disclosure is not limited to this. The diagnosis object image and the comparison candidate image need not necessarily be an image of the same patient and the same modality.

(Step S1010) <Acquisition of Diagnosis Object Image>

In Step S1010, the diagnosis object image acquiring unit 41 performs processing of acquiring a diagnosis object image (first image) to be processed from the inspection image database 23. This processing is performed when an operation is received from a user via a GUI provided by the operation unit 35 and the display unit 36. By this processing, the diagnosis object image acquiring unit 41 reads the diagnosis object image from the inspection image database 23, and the medical information processing apparatus 10 stores the diagnosis object image by using the ROM 32, the RAM 33, the storage unit 34, and the like. In the embodiment, a case where a three-dimensional CT image including a plurality of two-dimensional cross-sectional images (tomographic images) is acquired as the diagnosis object image will be described as an example. However, the present disclosure is not limited to this, and can be a two-dimensional CT image, a plain X-ray image, an MRI image, a camera image of a lesion portion of the subject, and the like. The diagnosis object image has accompanying information such as an ID (patient ID) of a patient who is the subject, an inspection date, an imaged region, and imaging parameters.

(Step S1020) <Acquisition of Comparison Candidate Images>

In step S1020, the comparison candidate image acquiring unit 42 performs processing of acquiring a plurality of inspection images (comparison candidate images, candidate images), which will be candidates of comparison with the diagnosis object image acquired in step S1010, from the inspection image database 23. As an example of this processing, the comparison candidate image acquiring unit 42 acquires inspection images of the same patient of the diagnosis object image from among the plurality of inspection images recorded in the inspection image database 23 as the comparison candidate images. Specifically, the comparison candidate image acquiring unit 42 acquires inspection images having the same patient ID as the patient ID that is the accompanying information of the diagnosis object image as the accompanying information by using a search function provided in the inspection image database 23.

The method of acquiring the comparison candidate images is not limited to the method described above. For example, the comparison candidate image acquiring unit 42 can refer to the inspection date of the diagnosis object image and acquire inspection images older than (earlier than) the diagnosis object image. Alternatively, the comparison candidate image acquiring unit 42 can refer to the accompanying information such as the imaging condition of the diagnosis object image and acquire inspection images captured with the same imaging condition as that of the diagnosis object image. Alternatively, the comparison candidate image acquiring unit 42 can acquire images of the same modality as that of the diagnosis object image, images captured by the same type of apparatus that has captured the diagnosis object image, images captured in the same medical institution where the diagnosis object image is captured, images captured with the same or similar imaging condition as that of the diagnosis object image, and the like as the comparison candidate images.

In the embodiment, the inspection images, which were captured at time points prior to the time point when the diagnosis object image was captured and which were captured with the same modality (CT apparatus in a specific example of the embodiment) as that of the diagnosis object image, are acquired as the comparison candidate images by the method described above. Hereinafter, the acquired comparison candidate image is written as I_r, i ($1 \le i \le N$). Here, N represents the number of the comparison candidate images acquired in this step. In the embodiment, a case of N=3 is used as a specific example.

When the number N of the comparison candidate images captured in this step is one, the processing of steps S1025 to S1040, described later, is omitted, the acquired comparison candidate image is regarded as a set of comparison images described later, and the processing of S1050 and subsequent steps is performed.

(Step S1025) <Generation of Combinations of Comparison Candidate Images>

In step 1025, the combination generation unit 43 generates combinations of N comparison candidate images acquired in step S1020. The combination generation unit 43 corresponds to an example of a setting unit that sets a plurality of combinations, each of which includes two or more candidate images from among a plurality of candidate images. In the embodiment, an example will be illustrated where a combination of comparison candidate images is generated as a combination of two different comparison candidate images. As a specific example of N=3, the combination generation unit 43 generates the following three combinations: <I_r, 1, I_r, 2>, <I_r, 1, I_r, 3>, and <I_r, 2, I_r, 3>. In the embodiment, the combination of comparison candidate images is written as P_j ($1 \le j \le M$). Here, M is a total number of the combinations. In the embodiment, a case of M=3 is used as an example in the description below. When the number of combinations of comparison candidate images generated in this step is one, the processing of steps S1030 and S1040 described later can be omitted and the processing is advanced to step S1050.

(Step S1030) <Calculation of Evaluation Value>

In step S1030, the evaluation unit 44 performs processing of calculating an evaluation value related to comparison with the diagnosis object image for each of the combinations of comparison candidate images generated in step S1025. In the embodiment, a case where the evaluation value is calculated based on the magnitude of an overlap range (common imaging range) between an imaging range of a combination of comparison candidate images to be evaluated and an imaging range of the diagnosis object image will be described as a specific example.

Processing of this step will be described in detail with reference to FIGS. 3 to 6.

Figure 3:
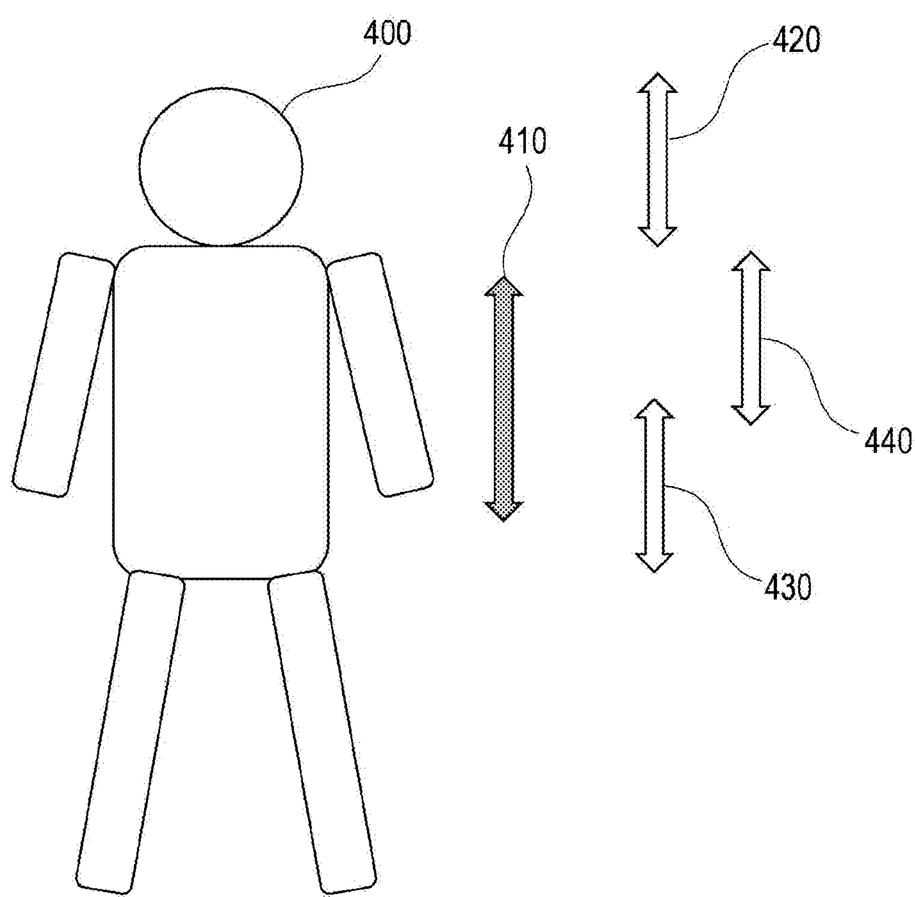
FIG. 3 is a diagram for explaining in detail processing of step S1030 in the embodiment.

In FIG. 3, reference numeral 400 indicates the subject in the embodiment. Reference numeral 410 indicates a range in a body axial direction of the subject in the imaging range of the diagnosis object image acquired in step S1010. Here, a case is shown where the imaging range of the diagnosis object image includes a range from the chest to the abdomen of the subject 400. In FIG. 3, reference numerals 420, 430, and 440 respectively indicate imaging ranges of the comparison candidate images I_r, 1, I_r, 2, and I_r, 3 (in the body axial direction) which are acquired in step S1020. Here, a case is shown where I_r, 1 is a comparison candidate image obtained by capturing an image of the head of the subject, I_r, 2 is a comparison candidate image obtained by capturing an image of the abdomen of the subject, and I_r, 3 is a comparison candidate image obtained by capturing an image of the chest of the subject.

Figure 4:
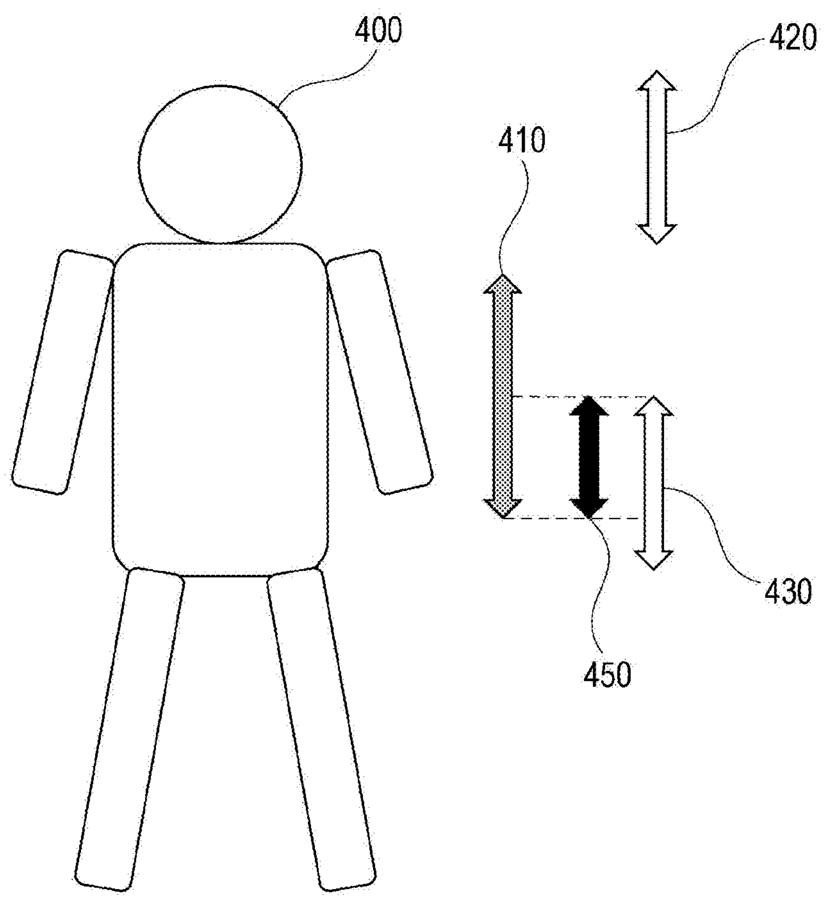
FIG. 4 is a diagram for explaining in detail the processing of step S1030 in the embodiment.

In FIG. 4, reference numeral 450 indicates an overlap range between an imaging range (range of the sum of the range 420 and the range 430) of a combination P_1 of comparison candidate images (combination of the comparison candidate images I_r, 1 and I_r, 2) and the imaging range 410 of the diagnosis object image. In other words, the range 450 represents a range where comparison processing between the diagnosis object image and an image can be performed by using the combination P_1 of comparison candidate images. FIG. 4 indicates that the imaging ranges of the diagnosis object image and the comparison candidate image I_r, 1 do not overlap and the imaging ranges of the diagnosis object image and the comparison candidate image I_r, 2 partly overlap. Therefore, the overlap of the imaging ranges of the diagnosis object image and the comparison candidate image I_r, 2 is the overlap range between the diagnosis object image and the combination P_1 of comparison candidate images.

Figure 5:
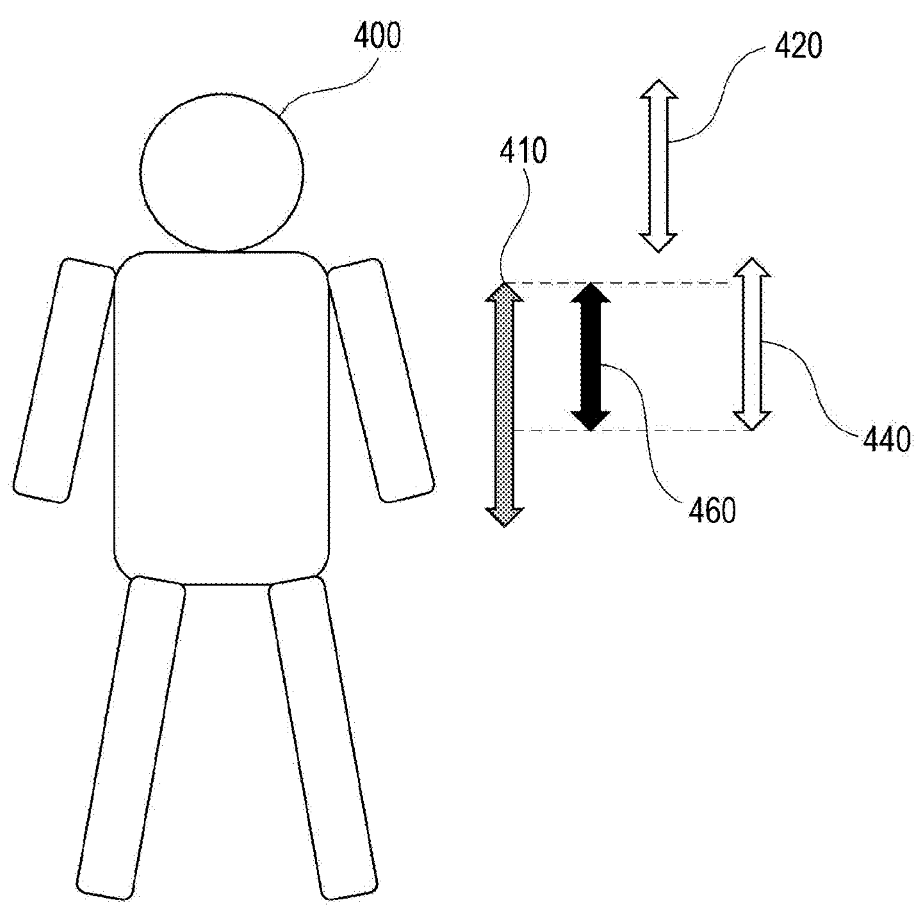
FIG. 5 is a diagram for explaining in detail the processing of step S1030 in the embodiment.

In FIG. 5, reference numeral 460 indicates an overlap range between an imaging range (range of the sum of the range 420 and the range 440) of a combination P_2 of comparison candidate images (combination of the comparison candidate images I_r, 1 and I_r, 3) and the imaging range 410 of the diagnosis object image in a similar manner as in FIG. 4. FIG. 5 indicates that the imaging ranges of the diagnosis object image and the comparison candidate image I_r, 1 do not overlap and the imaging ranges of the diagnosis object image and the comparison candidate image I_r, 3 partly overlap. Therefore, the overlap of the imaging ranges of the diagnosis object image and the comparison candidate image I_r, 3 is the overlap range between the diagnosis object image and the combination P_2 of comparison candidate images.

Figure 6:
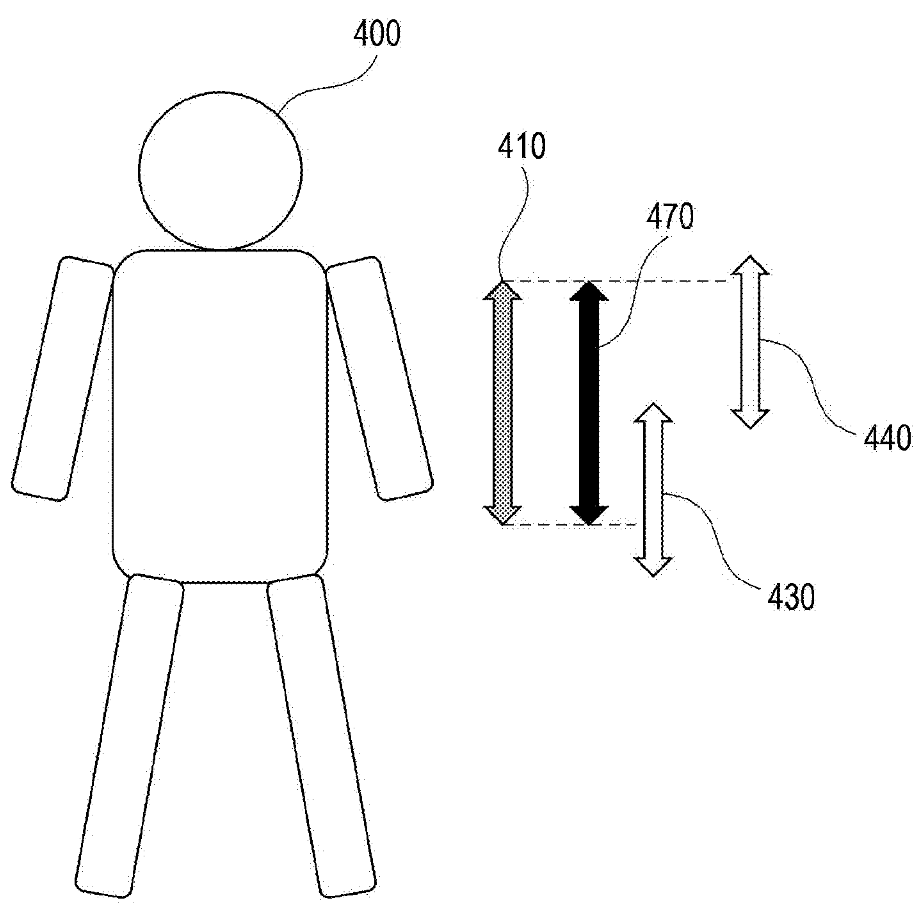
FIG. 6 is a diagram for explaining in detail the processing of step S1030 in the embodiment.

In FIG. 6, reference numeral 470 indicates an overlap range between an imaging range (range of the sum of the range 430 and the range 440) of a combination P_3 of comparison candidate images (combination of the comparison candidate images I_r, 2 and I_r, 3) and the imaging range 410 of the diagnosis object image in a similar manner as in FIG. 4. FIG. 6 indicates that the imaging range 410 of the diagnosis object image and a part of the imaging ranges 430 and 440 of the comparison candidate images I_r, 2 and I_r, 3 overlap. In this step, the evaluation unit 44 calculates the size of a range (overlap range) of each of the range 450 in FIG. 4, the range 460 in FIG. 5, and the range 470 in FIG. 6, and calculates an evaluation value E_j ($1 \leq j \leq M$) for each combination of comparison candidate images based on the sizes of the overlap ranges. The evaluation value E_j can be a length in the body axial direction of the subject of the overlap range as illustrated in FIGS. 4, 5, and 6, or may be a cubic content of the overlap range. Alternatively, the evaluation value E_j can be a rate of the overlap range with respect to the entire imaging range of the diagnosis object image. That is, the evaluation unit 44 corresponds to an example of an overlap range calculation unit that calculates an overlap range overlapping with a first image and an evaluation value calculation unit that calculates an evaluation value of each combination of a plurality of combinations based on the calculated overlap range. In particular, the evaluation unit 44 corresponds to an example of an overlap range calculation unit characterized by calculating an overlap range between a range of the sum of imaging ranges of two or more candidate images included in a combination and an imaging range of the first image.

The above description is premised on that a relative positional relationship between the imaging ranges of the diagnosis object image and the comparison candidate images is clear. When the relative positional relationship between the imaging ranges of the images is not clear, the medical information processing apparatus 10 performs positioning between the images, and thereby the relative positional relationship can be calculated. Any known method can be performed as the positioning processing, and the detailed description is omitted here.

The calculation of the relative positional relationship between the imaging ranges of the images is not limited to the method of positioning between images and can be calculated based on the accompanying information of each image. For example, when information of "imaged region" is attached to the diagnosis object image and the comparison candidate image, the positional relationship between the images can be calculated based on the information. For example, suppose that the accompanying information related to the imaged region of the diagnosis object image is "chest, abdomen," and the accompanying information related to the imaged region of the comparison candidate image I_r, 1 is "head." Suppose that the accompanying information related to the imaged region of the comparison candidate image I_r, 2 is "abdomen," and the accompanying information related to the imaged region of the comparison candidate image I_r, 3 is "chest." In this case, it is estimated that the imaging range of the combination P_1 of comparison candidate images (combination of the comparison candidate images I_r, 1 and I_r, 2) is "head and abdomen" and the overlap range overlapping with the diagnosis object image is "abdomen." It is estimated that the imaging range of the combination P_2 of comparison candidate images (combination of the comparison candidate images I_r, 1 and I_r, 3) is "head and chest" and the overlap range overlapping with the diagnosis object image is "chest." It is estimated that the imaging range of the combination P_3 of comparison candidate images (combination of the comparison candidate images I_r, 2 and I_r, 3) is "chest and abdomen" and the overlap range overlapping with the diagnosis object image is "chest and abdomen." In this case, the evaluation unit 44 can determine the number of regions included in the overlap range as the evaluation value (the number is one when the overlap range includes "chest" or "abdomen," and the number is two when the overlap range includes "chest and abdomen." A predetermined coefficient is set in advance for each region of a human body such as "chest" or "abdomen" and the evaluation value can be calculated by multiplying each overlap range described above by the coefficient. As a more specific example, for "chest," "abdomen," and the like, a standard size of the region in a human body is set as a coefficient. Thereby, it is possible to calculate the size of the overlap range by a simpler method and determine the size as the evaluation value.

By the method described above, the evaluation unit 44 performs the processing of step S1030 and calculates the evaluation value E_j ($1 \leq j \leq M$) for each combination P_j of comparison candidate images generated by step S1025.

(Step S1040) <Selection of Set of Comparison Images>

In step S1040, the selection unit 45 performs processing of selecting a combination of comparison candidate images suitable for comparison with the diagnosis object image from among M combinations of comparison candidate images based on each evaluation value calculated in step S1030. Specifically, the selection unit 45 selects a combination whose evaluation value is the highest among the evaluation values $E_j$ ($1 \le j \le M$) for the M combinations of comparison candidate images. That is, the selection unit 45 corresponds to an example of a second selection unit that selects at least one combination from a plurality of combinations based on the evaluation values. Then, the selection unit 45 selects each comparison candidate image included in a set of comparison images which is the selected combination of comparison candidate images. That is, the selection unit 45 corresponds to an example of a first selection unit that selects a second image, which will be compared with the first image, from among a plurality of candidate images. In particular, the selection unit 45 corresponds to an example of the second selection unit that is characterized by selecting two or more candidate images included in the selected combination as the second image.

(Step S1050) <Comparison Processing>

In step S1050, the image comparison unit 46 performs comparison processing between the diagnosis object image and a set of comparison images and calculates a comparison result. Specifically, for example, the image comparison unit 46 performs subtraction processing between images of the diagnosis object image and a set of comparison images and calculates a subtraction image as a comparison result. That is, the image comparison unit 46 corresponds to an example of a generation unit that generates a subtraction image, where a difference between the first image and the second image is drawn, by comparing the first image with the second image. In the embodiment, the set of comparison images is composed of a plurality of comparison images. As an example of processing method in this step, a method is considered where the image comparison unit 46 performs subtraction processing between each of the plurality of comparison images included in the set of comparison images and the diagnosis object image. In this case, subtraction images between each of the plurality of comparison images and the diagnosis object image are calculated and a set of these subtraction images can be a processing result of this step. It is desirable that the subtraction processing between the diagnosis object image and each of the plurality of comparison images is preformed after correcting differences between images that are not necessary for image diagnosis such as differences of positions and shapes of the subject drawn in the diagnosis object image and each of the plurality of comparison images and differences of image quality between images. The correction of differences between images can be performed by using any known method, and the detailed description thereof is omitted here. In the comparison processing, only the overlap ranges between the imaging ranges of each of the plurality of comparison images and the imaging range of the diagnosis object image can be processed. The overlap range can be easily acquired from processing results of step S1030 and step S1040, and thus the detailed description thereof is omitted. After a plurality of comparison images included in a set of comparison images are synthesized into one comparison image by stitching processing, comparison processing between the synthesized comparison image and the diagnosis object image can be performed.

The processing that calculates the comparison result is not limited to the subtraction processing described above. For example, the image comparison unit 46 can generate an overlapped image for the diagnosis object image and each image of a plurality of comparison images. In this case, different color channels are assigned to the diagnosis object image and the comparison image, and the overlapped image can be generated as a color image where the diagnosis object image and the comparison image are mixed.

(Step S1060) <Display of Comparison Result>

In step S1060, the display processing unit 47 performs processing of displaying the comparison result obtained by the processing of step S1050 on the display unit 36. As a specific example, the display processing unit 47 performs volume rendering on each of the diagnosis object image, a set of comparison images, and a set of subtraction images that is a comparison result. A method of arranging and displaying each of images created by the volume rendering (hereinafter referred to as volume rendering images) on the display unit 36 is considered. In this case, regarding the set of comparison images and the set of subtraction images, the display processing unit 47 may perform the volume rendering on each of a plurality of comparison images and subtraction images included in the set of comparison images and the set of subtraction images and arrange and display a plurality of volume rendering images. Besides this, for example, the display processing unit 47 can synthesize a plurality of images included in each set into one three-dimensional image by stitching processing based on the result of step S1050 or the like and thereafter perform the volume rendering.

The display method of the comparison result is not limited to the method described above, but the display processing unit 47 can display a two-dimensional cross-sectional image at an arbitrary position in each image on the display unit 36 and change the displayed two-dimensional cross-sectional image by an operation of a user. In this case, the display processing unit 47 identifies a corresponding position of each of the diagnosis object image and the set of comparison images based on the positional relationship between the diagnosis object image and the set of comparison images calculated in step S1030. It is desirable that the display processing unit 47 performs processing such as displaying a two-dimensional cross-sectional image of the corresponding position (processing of displaying a corresponding cross-section). Specifically, when the user changes a displayed two-dimensional cross-sectional image of the diagnosis object image, the display processing unit 47 displays a two-dimensional cross-sectional image at a position of the set of comparison images corresponding to a position of the two-dimensional cross-sectional image of the diagnosis object image on the display unit 36. When positioning between the diagnosis object image and the set of comparison images is performed in step S1050, it is desirable that the display processing unit 47 performs processing such as switching a displayed two-dimensional cross-sectional image of the diagnosis object image and a subtraction image by interlocking with the positioning based on a result of the positioning.

The processing of the medical information processing apparatus in the embodiment is performed by the procedure described above. According to the procedure, it is possible to select a plurality of comparison images that can be suitably compared with the diagnosis object image and provide a result of comparison processing of these images to the user without requiring the user to perform complicated operations.

Modified Example 1: Combination of Comparison Candidate Images <Number/Evaluation Based on the Number of Candidate Images>

In the processing of step S1025 of the embodiment, a case where two comparison candidate images are combined as a combination of comparison candidate images is described as an example. However, the implementation of the present disclosure is not limited to this. For example, three or more comparison candidate images can be combined. In this case, in the processing of step S1030, the evaluation unit 44 calculates the evaluation value by comparing an imaging range of a combination of the three or more comparison candidate images with the imaging range of the diagnosis object image. The number of comparison candidate images included in each combination of comparison candidate images can be a predetermined constant number or can be numbers different from each other. In this case, the greater the number of combined comparison candidate images, the larger the overlap range tends to be. Therefore, it is desirable that the evaluation value calculated in step S1030 is calculated based on the number of comparison candidate images included in the combination of comparison candidate images to be evaluated in addition to information of the overlap range described as the embodiment. For example, a method is considered where, when there are two combinations of comparison candidate images whose evaluation values by the overlap range are substantially the same (a difference between the evaluation values is smaller than a predetermined threshold value), the evaluation unit 44 raises higher the evaluation value of the combination of comparison candidate images having a smaller number of comparison candidate images. For example, a method can be employed where the selection unit 45 selects the combination of comparison candidate images having a smaller number of comparison candidate images as a set of comparison images from among combinations of comparison candidate images where the entire range of the diagnosis object image is the overlap range. Alternatively, a value obtained by multiplying the evaluation value based on the overlap range by a correction coefficient predetermined based on the number of comparison candidate images to be combined (the greater the number of images to be combined, the smaller the correction coefficient) can be used as an evaluation value after correction. Thereby, it is possible to perform the comparison processing of step S1050 on a smaller number of comparison images, so that there are effects of improving the efficiency of the processing of step S1050 and obtaining a higher quality comparison result.

Modified Example 2: Calculation Method of Evaluation Value <Image Quality/Imaging Condition>

In the processing of step S1030 in the embodiment, a case of calculating an evaluation value by an evaluation based on the overlap range between the imaging range of the diagnosis object image and the imaging range of the combination of comparison candidate images (hereinafter referred to as an overlap range evaluation) is described as an example. However, the implementation of the present disclosure is not limited to this.

For example, the evaluation unit 44 can calculate the evaluation value by performing an evaluation based on the image quality of each comparison candidate image included in the combination of comparison candidate images (hereinafter referred to as an image quality evaluation) aside from the overlap range evaluation and integrating evaluations of the overlap range evaluation and the image quality evaluation. That is, the evaluation unit 44 corresponds to an example of an image quality evaluation unit that evaluates the image quality of each candidate image included in a plurality of combinations. Specifically, the evaluation unit 44 estimates a noise level of each comparison candidate image included in each combination of comparison candidate images and lowers an evaluation value of a combination including a comparison candidate image whose noise level is high. For example, a value obtained by multiplying the evaluation value based on the overlap range evaluation by a correction coefficient predetermined based on a noise level of a comparison candidate image (the higher the noise level, the smaller the correction coefficient) can be used as an evaluation value after correction. At this time, it is desirable that the evaluation unit 44 calculates the size of the overlap range between each comparison candidate image and the diagnosis object image and calculates the evaluation value by placing more importance on a noise level of a comparison candidate image whose overlap range is large. The evaluation unit 44 can calculate the evaluation value by placing importance on a noise level of a comparison candidate image whose noise level is the highest among the comparison candidate images, at least a part of which overlaps with the imaging range of the diagnosis object image. Besides this, for example, when the image qualities of a plurality of comparison candidate images included in the same combination of comparison candidate images are different, the evaluation unit 44 can lower the evaluation value of the combination. For example, a value obtained by multiplying the evaluation value based on the overlap range evaluation by a correction coefficient predetermined based on the image quality of a comparison candidate image (the lower the evaluation value of the image quality, the smaller the correction coefficient) can be used as an evaluation value after correction.

In addition to the method described above, for example, the evaluation unit 44 can evaluate the comparison candidate image based on imaging conditions such as an image reconstruction function that is the accompanying information of the comparison candidate image, and a tube voltage value and a tube current value of an X-ray emission apparatus. That is, the evaluation unit 44 corresponds to an example of an imaging condition acquiring unit that acquires an imaging condition of each candidate image included in a plurality of combinations. The evaluation unit 44 can perform the evaluation based on the resolution of the comparison candidate image (pixel size and slice interval of a two-dimensional slice, and the like). For example, the evaluation unit 44 can correct the evaluation value to raise the evaluation value of a comparison candidate image whose slice interval is small.

In the above description, a method of performing the evaluation based on the image quality of the comparison candidate image is described as an example. However, in addition to the above, the evaluation can be performed based on the image quality of the diagnosis object image. For example, the evaluation unit 44 can evaluate the image quality of the diagnosis object image by the same method as that described above and calculate the evaluation value based on both evaluations of the evaluation of the image quality of the comparison candidate image and the evaluation of the image quality of the diagnosis object image. More specifically, it is possible to lower the evaluation value of a combination of comparison candidate images including a comparison candidate image whose image quality is lower than that of the diagnosis object image. In addition to the above, it is possible to raise the evaluation value of a combination of comparison candidate images including a comparison candidate image whose image quality is close to that of the diagnosis object image.

The evaluation unit 44 can acquire accompanying information such as an inspection purpose, a name of an organ to be inspected, and a name of a disease to be inspected of each comparison candidate image included in a combination of comparison candidate images from the inspection image database 23 as inspection information and evaluate the comparison candidate images based on the inspection information. For example, it is possible to correct the evaluation value to raise the evaluation value of a combination of comparison candidate images including a comparison candidate image having inspection information close to that of the diagnosis object image as the accompanying information. That is, the evaluation unit 44 corresponds to an example of an inspection information acquiring unit that acquires an inspection purpose, a name of an organ to be inspected, and/or a name of a disease to be inspected of an inspection, where each candidate image included in a plurality of combinations is captured, as the inspection information. A value obtained by multiplying the evaluation value by a correction coefficient predetermined based on a degree of coincidence between the accompanying information of the diagnosis object image and the accompanying information of the comparison candidate image (the lower the degree of coincidence, the smaller the correction coefficient) can be used as an evaluation value after correction.

The various corrections described above can be combined and used.

According to the method described above, there is an effect of obtaining a higher quality comparison result.

Modified Example 3: Selection Method

In step S1040 in the embodiment, a case where the selection unit 45 selects one combination of comparison candidate images whose evaluation value calculated in step S1030 is the highest is described as an example. However, the implementation of the present disclosure is not limited to this. For example, in step S1040, the selection unit 45 can select a plurality of combinations of comparison candidate images whose evaluation values are higher than a predetermined value as sets of comparison images. In this case, the image comparison unit 46 can perform the same comparison processing as that described above on each set of the plurality of sets of comparison images selected in step S1050 and output comparison results, the number of which is the same as the number of the sets of comparison images. According to the method described above, there is an effect that a user can arbitrarily select and observe a desirable comparison result from among the comparison results of a plurality of sets of comparison images that have cleared a predetermined condition.

Modified Example 4: Comparison Method

In the processing of step S1050 in the embodiment, a case where the image comparison unit 46 generates a subtraction image and an overlapped image as comparison processing between the diagnosis object image and a set of comparison images is described as an example. However, the implementation of the present disclosure is not limited to this. For example, the image comparison unit 46 performs deformation positioning processing on each of the comparison images included in the set of comparison images so that an anatomical structure drawn to each comparison image and an anatomical structure drawn to the diagnosis object image are substantially coincident with each other. Images obtained by deforming each comparison image based on a result of the deformation positioning processing can be a result of the comparison processing. Thereby, there is an effect that a user can easily grasp positions of comparison images included in a set of comparison images corresponding to a region to which the user pays attention in the diagnosis object image.

The implementation of the present disclosure is not limited to this. The processing of step S1050 can be omitted, and in step S1060, the display processing unit 47 can arrange and display the diagnosis object image and a set of comparison images on the display unit 36. At this time, it is desirable to display overlap ranges between comparison images included in the set of comparison images and the diagnosis object image in a manner where the user can visually recognize the overlap ranges based on a processing result of step S1030 or the like. Thereby, there is an effect that it is possible to display a set of comparison images selected as images suitable to be compared with the diagnosis object image from among a plurality of comparison candidate images in the same subject in a manner where the user can easily compare the set of comparison images with the diagnosis object image.

The medical information processing apparatus 10 can be configured to perform only processing for storing information for identifying a selected set of comparison images in the inspection image database 23 in association with the diagnosis object image. In this case, when observing the diagnosis object image by using another image viewer, it is possible to read the set of comparison images associated with the diagnosis object image and display the set of comparison images to be able to be compared with the diagnosis object image and it is possible to generate an overlapped image and a subtraction image between the diagnosis object image and the set of comparison images.

Modified Example 5: Storage with Association

In the embodiment, as the processing of step S1060, a case where the display processing unit 47 displays a comparison processing result between the diagnosis object image and a set of comparison images is described as an example. However, the implementation of the present disclosure is not limited to this. For example, the image comparison unit 46 can store the comparison result calculated in step S1050 into the inspection image database 23 and the control unit 37 can acquire the comparison result by an operation or the like from a user. Then, the display processing unit 47 can display the comparison result acquired from the inspection image database 23 by the same processing as that of step S1060. In this case, it is desirable that the control unit 37 stores the comparison processing result in association with the diagnosis object image acquired in step S1010 and the comparison images included in the set of comparison images selected in step S1040. This method is particularly effective in such a case where a long calculation time is required for the processing from step S010 to step S1050. In this case, the control unit 37 automatically performs a series of processing from step S1010 to step S1050 including the storing as batch processing. Thereby, the user can acquire the comparison result from the inspection image database 23 and display the comparison result at an arbitrary timing after the series of processing is completed.

Other Embodiments

Embodiment(s) can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While exemplary embodiments have been described, it is to be understood that the disclosure is not limited to the disclosed exemplary embodiments. The scope of the following claims is to be accorded the broadest interpretation so as to encompass all such modifications and equivalent structures and functions.

This application claims the benefit of Japanese Patent Application No. 2018-022068, filed Feb. 9, 2018, which is hereby incorporated by reference herein in its entirety.

What is claimed is:

1. An information processing apparatus for diagnosing an object, comprising:

an acquiring unit configured to acquire a first medical image of the object;

a first selection unit configured to select a second medical image of the object captured at a time different from the first medical image from a plurality of candidate images;

a comparison unit configured to compare the first medical image and the second medical image;

a setting unit configured to set a plurality of combinations including two or more candidate images from among the plurality of candidate images;

an overlap range calculation unit configured to calculate an overlap range that is a common imaging range between the first medical image and each combination of the plurality of combinations;

an evaluation value calculation unit configured to calculate an evaluation value of each combination of the plurality of combinations based on the calculated overlap range; and a second selection unit configured to select at least one combination from the plurality of combinations based on the evaluation value, wherein the first selection unit selects the two or more candidate images included in the selected combination as the second medical image.

2. The information processing apparatus according to claim 1, wherein the overlap range calculation unit calculates an overlap range between a range of a sum of imaging ranges of two or more candidate images included in the selected combination and an imaging range of the first medical image as the overlap range.

3. The information processing apparatus according to claim 1, wherein the evaluation value calculation unit calculates the evaluation value based on a size of the overlap range.

4. The information processing apparatus according to claim 1, further comprising:

an imaging condition acquiring unit configured to acquire an imaging condition of each of the candidate images included in the plurality of combinations, wherein the evaluation value calculation unit calculates the evaluation value based on the imaging condition.

5. The information processing apparatus according to claim 1, further comprising:

an image quality evaluation unit configured to evaluate an image quality of each of the candidate images included in the plurality of combinations, wherein the evaluation value calculation unit calculates the evaluation value based on the image quality.

6. The information processing apparatus according to claim 1, further comprising:

an inspection information acquiring unit configured to acquire, as inspection information, an inspection purpose, a name of an organ to be inspected, and/or a name of a disease to be inspected of an inspection, where each of the candidate images included in the plurality of combinations is captured, wherein the evaluation value calculation unit calculates the evaluation value based on the inspection information.

7. The information processing apparatus according to claim 1, further comprising:

a generation unit configured to generate a subtraction image, where a difference between the first medical image and the second medical image is generated by comparing the first medical image with the second medical image.

8. The information processing apparatus according to claim 1, wherein the first medical image and the candidate images are images captured from an identical patient.

9. An information processing method for diagnosing an object, comprising:

an inquiring step of acquiring a first medical image of the object;

a first selecting step of selecting a second medical image of the object captured at a time different form the first medical image from a plurality of candidate images;

a comparison step for comparing the first medical image and the second medical image;

a setting step of setting a plurality of combinations including two or more candidate images from among the plurality of candidate images;

an overlap range calculation step of calculating an overlap range that is a common image range between the first medical image and each combination of the plurality of combinations; an evaluation value calculation step of calculating an evaluation value of each combination of the plurality of combinations based on the calculated overlap range; and a second selection step of selecting at least one combination from the plurality of combinations based on the evaluation value, wherein the first selection step selects the two or more candidate images, which are included in the combination selected in the second selection step, as the second image.

10. The information processing apparatus according to claim 1, wherein the first medical image and the second medical image are three-dimensional volume images of an object, and the overlap range is a range in a direction of a body axial direction of the object.

11. The information processing method according to claim 9, wherein the first medical image and the second medical image are three-dimensional volume images of an object, and the overlap range is a range in a direction of a body axial direction of the object.

* * * * *